United States Patent [19]

Brooks et al.

[11] Patent Number: 4,797,275

[45] Date of Patent: Jan. 10, 1989

[54] NICARBAZIN FEED PREMIX

[75] Inventors: Norman D. Brooks, Greenfield; Rebecca A. Kenyon, Indianapolis; Peter W. Vanevenhoven, West Terre Haute, all of Ind.

[73] Assignee: Eli Lilly and Company, Indianapolis, Ind.

[21] Appl. No.: 780,352

[22] Filed: Sep. 26, 1985

[51] Int. Cl.⁴ .................... A61K 31/74; A61K 31/505
[52] U.S. Cl. ........................................ 424/78; 514/274
[58] Field of Search ............................ 514/274; 424/78

[56] References Cited

U.S. PATENT DOCUMENTS

| | | | |
|---|---|---|---|
| 2,731,382 | 1/1956 | Basso et al. | 514/274 |
| 3,379,554 | 4/1968 | Brindamour | 117/33 |
| 3,617,299 | 11/1971 | Mattoon et al. | 99/2 R |
| 4,096,239 | 6/1978 | Katz et al. | 424/21 |
| 4,132,753 | 1/1979 | Blichare et al. | 264/25 |
| 4,180,560 | 12/1979 | Katz et al. | 424/21 |

FOREIGN PATENT DOCUMENTS

| | | |
|---|---|---|
| 2441942 | 3/1976 | Fed. Rep. of Germany . |
| 2522483 | 12/1976 | Fed. Rep. of Germany . |
| 56-063925 | 5/1981 | Japan . |
| 56-065802 | 6/1981 | Japan . |
| 59-193811 | 11/1984 | Japan . |
| 603162 | 5/1979 | U.S.S.R. . |

OTHER PUBLICATIONS

Blodinger, *Formulation of Veterinary Dosage Forms*, Marcel Dekker, Inc., New York and Basel, 1983, pp. 158 and 159.

Friedman, et al., *C.A.* 91, 163008b (1979), Release Rate of Drugs From Ethyl Cellulose Coated Granules Containing Caffeine and Salicylic Acid.

*Primary Examiner*—Frederick E. Waddell
*Attorney, Agent, or Firm*—Joseph A. Jones

[57] ABSTRACT

This invention provides a novel formulation of an animal feed premix in substantially granular and non-dusty form comprising finely powdered nicarbazin and a water-soluble adjuvant having a melting point in the range from about 50° to about 85°.

11 Claims, No Drawings

NICARBAZIN FEED PREMIX

BACKGROUND OF THE INVENTION

Nicarbazin has long been sold and used as a coccidiostat for poultry. Infections by coccidia are extremely damaging to poultry in high-production facilities, and particularly to broiler chickens. Nicarbazin has been one of the most valuable coccidiostatic drugs for nearly thirty years.

Nicarbazin is not a single compound, but is a physical-chemical complex of 4,4'-dinitrocarbanilide with 2-hydroxy-4,6-dimethylpyrimidine. U.S. Pat. No. 2,731,382, of Basso and O'Neill, assigned to Merck and Company. It has been found that the particle size of nicarbazin has a great effect on its activity. Rogers, et al., *Science* 222, 630-32 (1983).

Accordingly, nicarbazin is always used for poultry medication in the form of a very fine powder, the particles of which range from a few tenths of a micron to a few microns in diameter. The fine particle size, which is necessary for best effect, accentuates a major processing difficulty of nicarbazin. It tends to develop strong electrostatic charges with handling. As a result, mixtures of nicarbazin with other substances tend to separate very easily, and the nicarbazin has a strong tendency to adhere to other surfaces and substances to which it is exposed.

The usual way to administer nicarbazin is in poultry feed, at a very low concentration such as 0.0125%. It is the custom to prepare a concentrated premix of animal drugs, which premix is then added to and mixed through batches of feed. Nicarbazin has caused important problems in handling because of its electrostatic properties. Mixed feed containing nicarbazin tends to separate, with the nicarbazin adhering to the walls of the equipment. As a result, the nicarbazin content of the treated feed is undesirably low, and other feed becomes contaminated with nicarbazin. Obviously, the situation is not desirable.

The present invention addresses the nicarbazin problem by providing an improved, non-separating feed premix.

SUMMARY OF THE INVENTION

The present invention provides an animal feed premix in substantially granular and non-dusty form comprising finely powdered nicarbazin and a water-soluble adjuvant having a melting point in the range from about 50° to about 85°.

DESCRIPTION OF THE PREFERRED EMBODIMENTS

Throughout the present document, all expressions of percentage, concentration and the like will refer to weight units unless otherwise stated. All temperatures are expressed in degrees Celsius.

The premix of the present invention is defined as substantially granular and non-dusty, and it is precisely those properties of the premix which make it more desirable, useful and convenient than have been previous nicarbazin premixes. The reader must understand that it is never possible to eliminate entirely any fine particles from a solid; the abrasion of handling and shipping, if nothing else, will create some fine particles. The examples which follow show that premixes according to the present invention typically contain less than 3-4% of particles smaller than 80-mesh, on the U.S. sieve scale (177 microns), and less than 2% of particles smaller than 100-mesh (149 microns). A premix of such a size range blends well with typical mixed poultry feeds, which have a similar size range. Nicarbazin does not tend to separate from the premix, nor does it tend to separate from feeds with which it is mixed.

Nicarbazin for use in the present premixes is prepared according to the best practice in the prior art. It has previously been known that nicarbazin complex must be in the form of a very fine powder, and the fact remains true for nicarbazin to be used in the present invention. The nicarbazin should have a typical particle size range such that about 50% of the particles are smaller than 10 microns.

It has been found that nicarbazin can be granulated without any adverse effect on its biological activity, with a water-soluble adjuvant having a melting point in the range from about 50° to about 85°. It appears that the water-soluble adjuvant, applied as a molten liquid to the nicarbazin, forms hard granules which break up rapidly in the bird's digestive tract, to release the nicarbazin particles in their original fine, unagglomerated form.

It appears to be important for the adjuvant to have a relatively sharp melting point, so that the mixed batch of nicarbazin and adjuvant becomes a nonsticky solid quickly upon cooling. Further, it is preferred for the adjuvant to be relatively hard, and even brittle, at ambient temperatures.

Animal feeds and feed premixes are often exposed to relatively high temperatures in storage, since such products are kept in barns and other uninsulated buildings. It is possible for storage temperatures in such buildings to approach 50° in hot weather. Accordingly, it is preferred to use an adjuvant with a higher melting point, for example, from about 65° to about 85°, particularly when the product is to be made or used in summer in a hot climate.

The preferred adjuvants are the polyethylene glycols (PEG) with a molecular weight range of from about 3,000 to about 12,000. The polyethylene glycols are well-established in pharmaceutical and agricultural chemistry; the best known brand name is Carbowax, of the Union Carbide Company. The most preferred polyethylene glycols are those with a molecular weight of from about 4,000 to about 8,000, and the most preferred grade is that with a molecular weight of about 8,000.

Further suitable adjuvants are chosen from the class of nonionic polyol surfactants. Many such polyols are in the suitable melting point range, and are entirely safe for use in animal feeds. Such classes as the block copolymers of propylene oxide and ethylene oxide; polymers of propylene and ethylene oxides on propoxylated ethylene diamine; and the straight chain oxyalkylated alcohols furnish suitable compounds. In general, the molecular weight of polyols should be about 6,000-10,000 in order to obtain the correct melting point range. Particular brand names of such products include but are not limited to the Pluronic, Tetronic and Plurafac series, all of BASF Wyandotte Corp., Parsippany, N.J.

The premix of the present invention may be made either with or without a carrier, as the formulator may desire in the circumstances. In the present sense, the term "carrier" refers to a granular, inert, physiologically-acceptable substance which provides a base to which the adjuvant adheres the nicarbazin. The most physically desirable and convenient carrier for such premixes is ground, granulated corn cob, which is readily available in the United States. Corn cob can be granulated in a particularly accurately sized and non-dusty form. Other carriers, however, such as granulated clay and the like may also be used.

Animal feed premixes have usually been prepared with a carrier of vegetable origin such as grain byproducts, solvent-extracted soybean feed, rice hulls, and such inexpensive substances. Such carriers are not particularly desirable for the present premixes, because they are not in themselves non-dusty and granular. Accordingly, if a carrier such as rice hulls is used, the adjuvant must not only granulate the nicarbazin, it must also granulate the rice hulls and the adjuvant is not efficiently used.

The concentration of nicarbazin in a feed premix of the present invention is not a critical factor. Obviously, feed of any appropriate concentration can be prepared from a premix of any higher concentration. Nicarbazin has conventionally been sold as a premix containing 25% active ingredient. Concentrations in that range, such as from about 10% to about 35%, are convenient and economical and are preferred. When a carrier is not used in the premix, the concentration of nicarbazin can conveniently be very high, such as in the range of about 60–80%.

Thus, the nicarbazin concentration in the premix may be in the range of about 5–80%, depending entirely on economics and convenience in the circumstances in which the premix is to be made and used.

The concentration of the adjuvant in a premix of the present invention need not be very high. Excellent premixes according to the present invention are made with adjuvant concentrations of about 5–20%, when a carrier is used and the nicarbazin concentration is in the preferred range of about 10–35%. When a carrier is not used, the adjuvant makes up the entire inert ingredient content, and therefore may be in high concentration. For example, if a 50% premix is made without a carrier, the adjuvant content is obviously 50%.

In general, it is necessary to use only an amount of the adjuvant sufficient to granulate the product and bind the nicarbazin so that it cannot release dust in handling. The examples below illustrate many useful premixes and demonstrate the manner in which the necessary amount of adjuvant is determined. The most preferred amount of adjuvant, however, will usually be found in the range from about 5% to about 20%, when an appropriate carrier is used in the formulation.

The amount of carrier in the premix is the remainder, after the desired concentration of nicarbazin and the necessary amount of adjuvant have been determined. The amount of carrier has no bearing on the physical acceptability of the premix; entirely satisfactory premixes have been prepared with no carrier at all, and as much as 80% of carrier may be used when the concentration of nicarbazin is low. The determination of the amount of carrier is easily made by a formulations chemist.

In some instances, it has been found to be advantageous to add a relatively small amount of an inert oil, such as a vegetable oil or, more preferably, a light mineral oil, to the carrier before adding the adjuvant and nicarbazin. It is believed that a small amount of oil, in the general range of about 2–20%, helps to seal the crevices and pores of the carrier, and thereby allows a desirable product to be made with a smaller amount of the more expensive adjuvant. The addition of an oil is not particularly important when corn cob carrier is used, but becomes more important when a carrier such as a clay or diatomaceous earth is chosen. Such carriers have a great capacity to absorb liquids, and will require a large amount of adjuvant to make a satisfactory product. Accordingly, when such carriers are to be used, it is more convenient to preload the carrier with an inexpensive inert oil.

The manner in which the premixes are prepared is important. It is necessary to melt the adjuvant, and to mix the adjuvant with the nicarbazin and the carrier, if one is used, in such a manner that the nicarbazin is well dispersed.

When a carrier is used, it is best to add the carrier to a suitable mixer and heat it to above the melting point of the adjuvant. The adjuvant is then added, as a solid or a liquid, and mixing is continued until the adjuvant is well spread over the surface of the carrier particles. Then the nicarbazin is added and mixing is continued until the nicarbazin is well spread through the mass of the product. The mixed product is then cooled to below the melting point of the adjuvant.

The mixer used for the preparation must provide enough mixing power and shear to disperse the agglomerates which nicarbazin invariably forms because of its fine, highly charged character. The best type of mixer is one which combines mass movement, effected by rotating plows or ribbons, with high-speed mixing. The desired action can be obtained by installing a high-speed rotating blade in the side of a ribbon or plow-type solids mixer.

When a carrier is not used, the preparation of the premix is a conventional operation. The appropriate amount of nicarbazin is dispersed in molten adjuvant, and the mixture is cooled and granulated in such a manner that it cannot separate before it cools. For example, flaking on a drum or belt-type chiller is appropriate. The resulting flakes are then further chopped or broken and screened to select the desired particle size. Such operations are commonly used in many industries.

It will be understood that, no matter what process is used and whether a carrier is included or not, the final step of manufacture must be screening to separate over-size and under-size particles. Undersize may be simply recycled to the mixer, and over-size may be recycled or may be lightly ground, and then recycled to the final screening operation.

The following examples are provided further to illustrate and explain the premixes of the present invention and the processes by which they are made.

EXAMPLE 1

This test was carried out in a 10 cubic foot horizontal mixer equipped with a rotating plow agitator, and having a 3600-rpm. rotating blade chopper installed in its sides. To the mixer was added 65.0 kg. of 40–60 mesh (U.S. sieve) granulated corn cob, and the mixer was heated, by means of a steam jacket, until the temperature of the corn cob was about 70°. To it was then added 10.9 kg. of polyethylene glycol, molecular weight about 8,000, and the batch was mixed for 5 minutes more, at increased speed. To it was added 33 kg. of nicarbazin. The batch was mixed for a total of 35 minutes, at the end of which time the bulk temperature was 67°. The product was discharged from the mixer into pans where it was allowed to cool. Its density was 33.8 lb./ft.$^3$. When the product had cooled, it was dumped from the pans into drums and a sample was taken for sieve analysis, on standard U.S. sieves.

| | |
|---|---|
| +20 | 0.0% |
| +40 | 3.59% |
| +80 | 95.27% |
| +100 | 0.76% |
| −100 | 0.38% |

EXAMPLE 2

To the same type of mixer described in Example 1 was added 60 kg. of 40–60 mesh granular corn cob, and the mixer was heated until the bulk temperature was 70°–77°. The corn cob was mixed at 74–80 rpm. To the mixer was then added 10 kg. of polyethylene glycol, molecular weight about 3,350, and the mixture was agitated for 5 minutes. To it was then added 30 kg. of nicarbazin, and the side chopper of the mixer was started. The batch was mixed and chopped for 10 minutes, at which time the bulk temperature of the batch was 90°. The product was emptied from the mixer into flat pans, which were cooled in the open air on a cool spring day. A sieve analysis of the product was performed, with the following results.

| | |
|---|---|
| +20 | 0.0% |
| +40 | 2.0 |
| +80 | 95.4 |
| +100 | 1.2 |
| −100 | 1.4 |

EXAMPLE 3

A 60 g. portion of nicarbazin was added to 40 g. of molten polyethylene glycol of molecular weight about 4,000. The nicarbazin was thoroughly dispersed through the molten PEG by hand, and the resulting slurry was cooled in a thin sheet in a metal pan. The cooled sheet was broken into flakes, and the flakes were granulated by hand to produce a granular product of approximately 30–80 mesh.

EXAMPLE 4

A 85 g. portion of nicarbazin was placed in a porcelain mortar, and to it was added 15 g. of molten polyethylene glycol 4,000. The mixture was briskly agitated by hand and agitation was continued while the mixture cooled, so that the product cooled in granular form. When it had reached ambient temperature, the mixture was screened to isolate 30 g. of the desired 30–80 mesh portion.

EXAMPLE 5

To a 2-liter ribbon blender was added 272.4 g. of granular corn cob, 30–100 mesh size range. The mixer was heated, 45.4 g. of polyethylene glycol, molecular weight about 3,350, was added, and that mixture was heated to 65°. Then 136.2 g. of nicarbazin was added and the mixture was agitated until it was homogeneous. The premix was then emptied from the mixer and cooled. Only a very small amount of dust was visible. The sieve analysis was as follows.

| | |
|---|---|
| +30 | 1.4% |
| +100 | 96.8 |
| −100 | 1.8 |

EXAMPLE 6

The 2-liter ribbon blender was charged with 274.6 g. of 30–100 mesh corn cob, 9.1 g. of light mineral oil and 34.1 g. of polyethylene glycol, molecular weight about 3,350. The mixture was heated to 65°, and was mixed until homogeneous. Then 136.2 g. of nicarbazin was added, and the mixer was run until the mixture was homogeneous. The batch was cooled to 35° with continued mixing, and the mixer was emptied. A very small amount of dust was visible upon pouring the batch of premix.

EXAMPLE 7

The 2-liter ribbon blender was used to prepare a batch, made as described in Examples 5 and 6, but made up of 227.0 g. of 40–60 mesh corn cob, 45.4 g. of polyethylene glycol of molecular weight 3,350, and 181.6 g. of nicarbazin. Thus, a 40% premix was prepared. The cooled batch, containing 40% nicarbazin, was elegant in free-flowing granular form with very little visible dust.

The following additional exemplary formulations of premixes according to the present invention are provided to assure the understanding of the reader. All of the products which are briefly described in the following table are made in the same type of equipment and with the same order of addition which has been described in the Examples above.

| Example | % Nicarbazin | Carrier, mesh size | % Light Mineral Oil | Adjuvant | % Adjuvant |
|---|---|---|---|---|---|
| 8 | 5 | Diatomaceous earth, 30/60 | 20 | PEG 3,000 | 12 |
| 9 | 10 | Montmorillonite, 30/80 | 20 | PEG 12,000 | 10 |
| 10 | 15 | Attapulgite, 40/60 | 20 | PEG 4,000 | 15 |
| 11 | 20 | Corncob, 20/40 | 0 | PEG 6,000 | 10 |
| 12 | 25 | Corncob, 40/80 | 0 | PEG 10,000 | 8 |
| 13 | 35 | Diatomaceous earth, 40/80 | 15 | PEG 4,000 | 15 |
| 14 | 45 | Attapulgite, 30/60 | 10 | PEG 8,000 | 17 |
| 15 | 50 | Montmorillonite, 30/80 | 10 | PEG 8,000 | 10 |
| 16 | 60 | Corncob, 40/80 | 0 | PEG 6,000 | 7 |
| 17 | 70 | None | 0 | PEG 10,000 | 30 |
| 18 | 80 | None | 0 | PEG 8,000 | 20 |

We claim:

1. An animal feed premix in substantially granular and non-dusty form comprising from about 5% to about 80% of finely powdered nicarbazin and polyethylene glycol with a molecular weight range of from about 3,000 to about 12,000.

2. A premix of claim 1 comprising a carrier.

3. A premix of claim 1 wherein the concentration of nicarbazin is from about 10% to about 35%.

4. A premix of claim 1 wherein the melting point of the polyethylene glycol is from about 65° to about 85° C.

5. A premix of claim 2 wherein the melting point of the polyethylene glycol is from about 65° to about 85° C.

6. A premix of claim 3 comprising a carrier and wherein the melting point of the polyethylene glycol is from about 65° to about 85° C.

7. A premix of claim 1 which does not comprise a carrier.

8. A premix of claim 7 wherein the concentration of nicarbazin is from about 60% to about 80%.

9. A premix of claim 2 wherein the carrier is granulated corncob.

10. A premix of claim 3 wherein the carrier is granulated corncob.

11. A premix of claim 6 wherein the carrier is granulated corncob.

* * * * *